United States Patent [19]
Cliffe et al.

[11] Patent Number: 5,369,103

[45] Date of Patent: * Nov. 29, 1994

[54] PIPERAZINE DERIVATIVES

[75] Inventors: Ian A. Cliffe, Slough; Alan C. White, Englefield Green; Anderson D. Ifill, Didcot, all of England

[73] Assignee: John Wyeth & Brother, Limited, Maidenhead, England

[*] Notice: The portion of the term of this patent subsequent to Dec. 8, 2009 has been disclaimed.

[21] Appl. No.: 861,834

[22] Filed: Jun. 19, 1992

[30] Foreign Application Priority Data

Oct. 19, 1990 [GB] United Kingdom ............... 9022790

[51] Int. Cl.$^5$ ............... A61K 31/395; A61K 31/495; C07D 403/06; C07D 403/14
[52] U.S. Cl. ............... 514/211; 540/598; 544/360; 544/364; 544/372; 544/362; 544/375; 544/392; 514/210; 514/255; 514/235.8
[58] Field of Search ............... 540/598, 601; 544/121, 544/295, 360, 362, 363, 359, 372, 375, 357, 392, 364; 514/210, 211, 255, 235.8, 212

[56] References Cited

U.S. PATENT DOCUMENTS

| | | | |
|---|---|---|---|
| 4,921,958 | 5/1990 | Abou-Gharbia et al. | 544/295 |
| 4,988,814 | 1/1991 | Abou-Gharbia et al. | 544/295 |
| 5,169,845 | 12/1992 | Cliffe et al. | 544/121 |

FOREIGN PATENT DOCUMENTS 2227018 4/1989 United Kingdom.

OTHER PUBLICATIONS

March, Advanced Organic Chemistry (New York, McGraw-Hill Books, 1987) pp. 879-880.

*Primary Examiner*—Mukund J. Shah
*Assistant Examiner*—P. K. Sripada
*Attorney, Agent, or Firm*—Arthur G. Seifert

[57] ABSTRACT

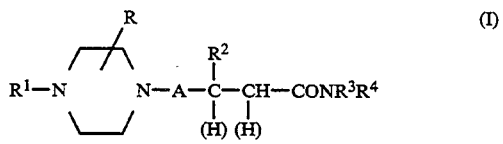

where A is an alkylene chain of 1 or 2 carbon atoms optionally substituted by one or more lower alkyl groups, R is hydrogen or lower alkyl, $R^1$ is a mono or bicyclic aryl or a heteroaryl radical, $R^2$ is an aryl radical, a heteroaryl radical, or an aryl-or heteroaryl-lower alkyl radical, $R^3$ is hydrogen, lower alkyl or aryl and $R^4$ is hydrogen, lower alkyl, cycloalkyl, cycloalkyl(-lower)alkyl, aryl, or aryl(lower)alkyl or $R^3$ and $R^4$ together with the nitrogen atom to which they are both attached represent a saturated heterocyclic ring which may contain a further hetero atom and the dotted line represents a single or double bond, the hydrogen atoms shown in brackets being present when the dotted line represents a single bond and their pharmaceutically acceptable acid addition salts are 5-HT$_{1A}$ binding agents which may be used, for example, for the treatment of CNS disorders such as anxiety.

4 Claims, No Drawings

PIPERAZINE DERIVATIVES

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

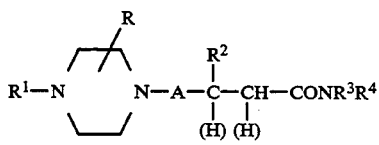

and the pharmaceutically acceptable acid addition salts thereof.

In formula (I)

A is an alkylene chain of 1 or 2 carbon atoms optionally substituted by one or more lower alkyl groups, R is hydrogen or lower alkyl, $R^1$ is a mono- or bi-cyclic aryl or a heteroaryl radical, $R^2$ is an aryl radical, a heteroaryl radical, or an aryl- or heteroaryl-lower alkyl radical, $R^3$ is hydrogen, lower alkyl or aryl and $R^4$ is hydrogen, lower alkyl, cycloalkyl, cycloalkyl(lower)alkyl, aryl, or aryl(lower)alkyl or $R^3$ and $R^4$ together with the nitrogen atom to which they are both attached represent a saturated heterocyclic ring which may contain a further hetero atom and the dotted line represents a single or double bond, the hydrogen atoms shown in brackets being present when the dotted line represents a single bond.

The term "lower" as used herein means that the radical referred to contains 1 to 6 carbon atoms. Preferably such radicals contain 1 to 4 carbon atoms. Examples of "lower alkyl" are methyl, ethyl, propyl, isopropyl, butyl, isobutyl, tert.-butyl, pentyl and isopentyl.

When used herein "aryl" means an aromatic radical having 6 to 12 carbon atoms (e.g. phenyl, naphthyl) which optionally may be substituted by one or more substituents commonly used in medicinal chemistry, eg substituents such as lower alkoxy, lower alkylthio halogen, trifluoromethyl, nitro, carbalkoxy, carboxamido, cyano, amino, (lower)alkylamino and di(lower)alkylamino.

Examples of aryl(lower)alkyl and aryl(lower)alkoxy include, for example, benzyl and benzyloxy in which the phenyl group may be substituted as defined above.

When $R^1$ is an aryl radical it is preferably a phenyl radical containing a substituent in at least one ortho position, eg o-(lower)alkoxyphenyl, or a naphthyl radical.

The term "heteroaryl" refers to an aromatic radical containing one or more hetero atoms (eg oxygen, nitrogen, sulphur) and which may be optionally substituted by one or more substituents. Examples of suitable substituents are given above in connection with "aryl" radicals. The heteroaryl radical may be mono- or bi-cyclic and contain, for example 5 to 11 ring atoms. A monocyclic radical may contain 5 to 7 ring atoms and a bicyclic radical may contain 9 to 11 ring atoms. When $R^1$ is heteroaryl it is preferably a monocyclic nitrogen containing radical such as optionally substituted pyridinyl, pyrimidinyl or pyrazinyl or a bicyclic radical such as quinolinyl or isoquinolinyl.

When $R^2$ is heteroaryl or heteroaryl-lower alkyl the "heteroaryl" group may be, for example a nitrogen containing heteroaryl radical (eg an optionally substituted pyridinyl, pyrimidinyl or pyrazinyl radical) or a heteroaryl radical containing, for example, an oxygen or sulphur atom as the hetero atom, eg thienyl or furyl.

A cycloalkyl group can contain 3 to 12 carbon atoms.

Examples of the radical —A— include —$CH_2$—, —$CH(CH_3)$——$C(CH_3)_2$—, —$CH_2$—$CH_2$—, —$CH(CH_3)$—$CH_2$—, —$CH_2$—$CH(CH_3)$—, —$C(CH_3)_2$—$CH_2$— and —$CH_2$ $C(CH_3)_2$—

When $R^3$ and $R^4$ together with the nitrogen atom to which they are attached form a heterocyclic ring this may be, for example, azetidino, pyrrolidino, piperidino, hexahydroazepino, morpholino or piperazino which may be optionally substituted by, for example, lower alkyl, aryl or aryl(lower)alkyl.

Preferred compounds are:

those in which A is —$CH_2$— those in which $R^1$ is aryl particularly an optionally substituted phenyl such as o-methoxyphenyl;

those in which R is hydrogen;

those in which $R^2$ is aryl particularly optionally substituted phenyl; and those in which —$NR^3R^4$ represents a cyclic grouping eg piperidino or hexahydroazepino.

The compounds of the invention may be prepared by a number of methods known in the art from known starting materials or starting materials that may be prepared by conventional methods. In one method for preparing an amide of formula (I), an amine of formula $$NHR^3R^4 \qquad (II)$$

where $R^3$ and $R^4$ are as defined above is acylated with an acid of formula

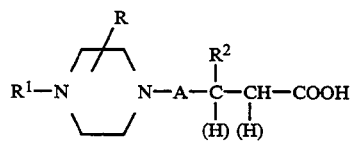

ps (where A, R, $R^1$ and $R^2$ are as defined above) or with an acylating derivative thereof. Examples of acylating derivatives include the acid halides (eg acid chlorides), azides, anhydrides, imidazolides (eg obtained from 1 , 1' carbonyldiimidazole), activated esters or 0-acyl ureas obtained from a carbodiimide such as a dialkylcarbodiimide particularly dicyclohexylcarbodiimide. Preferably the amine is acylated with the acid in presence of a coupling agent such as 1 , 1' -carbonyldiimidazole, isobutylchloroformate or diphenylphosphinyl chloride.

The acids of formula (III) may be prepared by known methods. For example they may be prepared by hydrolysis of a corresponding ester or nitrile. The ester or nitrile in which the dotted line represents a single bond may be obtained by reduction of a corresponding compound in which the dotted line represents a double bond. The ester in which the dotted line represents a double bond may be prepared by replacing the carbonyl oxygen of a ketone of formula

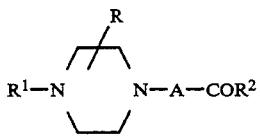 (IV)

with the appropriate olefinic group. For example the ketone may be reacted with an appropriately substituted α-silylated carbanion according to the Peterson Reaction. The carbanion may contain the ester group or a nitrile group which may be subsequently hydrolysed to the desired acid group after carrying out the Peterson Reaction.

The compounds of the invention in which the dotted line represents a double bond may be obtained directly by a reaction on a ketone of formula (IV) using an olefination agent containing the group —CONR$^3$R$^4$. For example, the olefination may be carried out by means of a Peterson reaction using, for example, an α-silylated carbanion derived from a silyl compound of formula

 (V)

(where neither R$^3$ nor R$^4$ are hydrogen and each R$^5$ is independently an alkyl group). Preferably each R$^5$ is methyl. In an alternative method of olefination, the compound (IV) may be reacted with a phosphonate carbanion eg a compound of formula

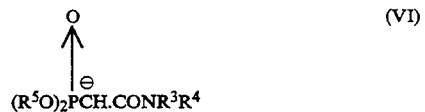 (VI)

The reaction may be carried out according to Wadsworth/Emmons modification of the Wittig reaction (see J. Am. Chem. Soc. 1961, 83, 1733).

The compounds of the invention in which the dotted line represents a single bond may be prepared by reduction of the compound of the invention in which the dotted line represents a double bond. The reduction may be carried out by, for example, a dissolving metal reduction, eg magnesium in methanol or by catalytic hydrogenation.

An alternative method of preparing the compounds of the invention comprises alkylation of a piperazine of formula

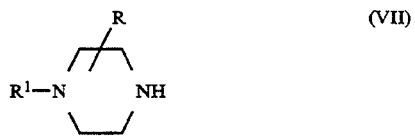 (VII)

(where R and R$^1$ are as defined above) with an alkylating agent providing the group

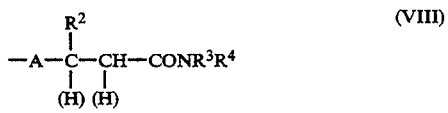 (VIII)

(where A, R$^2$, R$^3$, R$^4$ and the dotted line are as defined above).

The alkylating agent may be, for example, a compound of formula

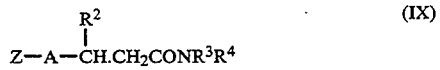 (IX)

where A, R$^2$, R$^3$ and R$^4$ are as defined above and Z is a leaving group such as halogen or an alkyl- or aryl-sulphonyloxy group.

The compounds of the invention where R$^3$ is hydrogen and R$^4$ is a secondary or tertiary lower alkyl group or a cycloalkyl group may be prepared by reacting a nitrile of formula

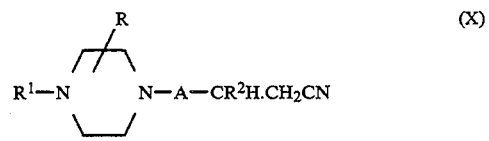 (X)

where R, R$^1$, R$^2$ and A are as defined above, with a secondary or tertiary alcohol of formula

where R$^4$ is as defined immediately above or with an olefin of formula

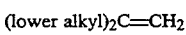

The reaction may be carried out in a strongly acidic medium according to the Ritter Reaction.

The nitriles of formula (X) may be prepared in a similar manner to the method described above for the corresponding esters from the ketones of formula (IV).

The compounds of the invention where R$^2$ is an electron withdrawing heteroarvl radical [eg 2-pyridyl, 4-pyridyl or a 1-substituted-2-imidazolyl (eg a N-protected-2-imidazolyl such as 1-ethoxymethyl-2-imidazolyl-]and the dotted line represents a single bond may be prepared by an alternative method which comprises forming an anion of a compound of formula

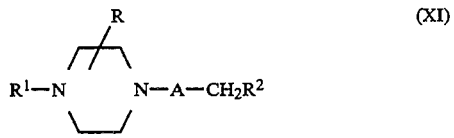 (XI)

and R, R$^1$ and A are as defined above and R$^2$ is as defined immediately above and reacting the anion with a compound of formula

where R$^3$ and R$^4$ are as defined above and Y is a leaving group such as halogen. The anion may be prepared by reacting the compound of, formula XI with a base eg n-butyl lithium.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

Some compounds of the invention (for example, those in which the dotted line represents a single bond) contain one or more asymmetric carbon atoms, so that such compounds can exist in different steroisomeric forms. The compounds can be, for example, racemates or optically active forms. The optically active forms can be obtained by resolution of the racemates or by asymmetric synthesis. The compounds of the invention in which the dotted line represents a double bond can exist in the form of geometrical isomers. Some methods of preparation give predominately one or other isomer (for example a Peterson reaction on compound IV can give predominantly the E or Z isomer depending upon the reaction conditions) while others give mixtures of isomers which can be separated by chromatography. The preferred isomers are the E-isomers.

The compounds of the present invention possess pharmacological activity. In particular, they act on the central nervous system by binding to 5-HT receptors. In pharmacological testing it has been shown that the compounds particularly bind to receptors of the $5HT_{1A}$ type. In general, the compounds selectively bind to receptors of the $5HT_{1A}$ type to a much greater extent than they bind to other receptors such as $\alpha_1$. Many exhibit activity as $5HT_{1A}$ antagonists in pharmacological testing. The pharmacological testing of the compounds indicates that they can be used for the treatment of CNS disorders, such as anxiety in mammals, particularly humans. They may also be useful as antidepressants, hypotensives and as agents for regulating the sleep/wake cycle, feeding behaviour and/or sexual function.

The compounds of the invention were tested for $5HT_{1A}$ receptor binding activity in rat hippocampal membrane homogenate by the method of B. S. Alexander and M. D. Wood, J Pharm Pharmacol, 1988, 40,888-891. The results for representative compounds of the invention are given below

|  | $IC_{50}$ (nm) |
|---|---|
| Compound of Example 3 (E-isomer) | 9 |
| Compound of Example 6 | 1.38 |

The affinity for $\alpha_1$ sites (as measured by the procedure of A. L. Marrow et al, Mol. Pharmacol., 1986, 29, 321 ) for the above compounds is given below

|  | $IC_{50}$ (nm) |
|---|---|
| Compound of Example 3 (E-isomer) | 2160 |
| Compound of Example 6 | 682 |

The compounds are tested for $5HT_{1A}$ receptor antagonism activity in a test involving the antagonism of 5-carboxamidotryptamine in the guinea-pig ileum in vitro (based upon the procedure of Fozard et al, Br J Pharmac, 1985, 86, 601P). The compound of Example 6 shows a $pA_2$ of 9.1

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols, eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

E, Z-Methyl 4-[4-(2-methoxyphenyl)piperazin-1-yl]-3-phenylbut-2-enoate n-Butyllithium (1.35 M, 35.9 mmol) was added slowly to a cooled (-78° C.) solution of diisopropylamine (3.62 g, 35.8 mmol) in dry tetrahydrofuran (40 ml). After stirring at this temperature for 15 min., a solution of methyl trimethylsilylacetate (5.00 g, 34.2 mmol) in dry tetrahydrofuran (10 ml) was added dropwise. The reaction mixture was stirred at −70° C. for 20 min. and a solution of 1-(2-methoxyphenyl)-4-(2-oxo-2-phenylethyl)piperazine (10.59 g, 34.2 mmol) in dry tetrahydrofuran ( 70 ml ) was added dropwise, maintaining the temperature of the reaction mixture below −60° C. The reaction mixture was stirred at −70° C. for 1 h and then allowed to warm to room temperature overnight. Ammonium chloride (10%, 100 ml) was added to the ice-cooled reaction mixture and the tetrahydrofuran removed under reduced pressure. The aqueous residue was extracted with dichloromethane (3×70 ml) and the combined organic phases washed with brine (70 ml), water (70 ml), dried (MgSO₄) and concentrated to afford a brown oil. The oil was chromatographed on silica gel, eluting with light petroleum: ethyl acetate (2:1 to 1:1 ) to afford an oil (7.56 g) which partially solidified on standing. A sample of the oil (1.72 g) was dissolved in ethyl acetate and acidified with ethereal hydrogen chloride to afford the title compound as the dihydrochloride (1.60 g), m.p. 164.6°–166.7° C. NMR indicated a 1:1 mixture of E and Z isomers.

EXAMPLE 2

4-[4-(2-methoxyphenyl)piperazin-1-yl]-3-phenylbut-2-enoic acid

E, Z-Methyl 4-[4-(2-methoxyphenyl)piperazin-1-yl]-3-phenylbut-2-enoate (E:Z ratio 1:1) (9.50 g, 26.0 mmol) in concentrated hydrochloric acid was heated under reflux for 1 h and the reaction mixture concentrated under reduced pressure to afford an off-white foam. The crude product was triturated with acetone to afford a colourless powder (7.38 g) and a sample (1.08 g) was recrystallised from diisopropyl ether-ethanol to afford the title compound as the dihydrochloride, m.p 212.0° to 213.6°.

The sample contains 90% of the E isomer and 10% of the Z isomer.

EXAMPLE 3

2,3,4,5,6,7-Hexahydro-1-[4-(4-(2-methoxyphenyl)piperazin-1-yl)-3-phenylbut-2-enoyl]-1H-azepine Oxalyl chloride (3.50 ml) was added to a suspension of 4-[4-(2-methoxyphenyl)piperazin-1-yl]-3-phenylbut-2-enoic acid dihydrochloride (4.17 g, 9.81 mmol) in dichloromethane (50 ml) and a few drops of dry N,N-dimethyl formamide added. After stirring at room temperature for 3 h, the solid formed was filtered off and a solution of triethylamine (3.07 g, 30.4 mmol) and hexamethyleneimine (1.07 g, 10.8 mmol) in dichloromethane (25 ml) was added dropwise to an ice-cooled suspension of the filtered solid in dichloromethane (50 ml). The reaction mixture was stirred at room temperature for 2 h and then concentrated under reduced pressure. The crude product was chromatographed on silica gel, eluting with ethyl acetate: pentane (1:1 to 2:1) to afford the title compound as two isomers. The Z-isomer was obtained as an oil and this was dissolved in diethyl ether and acidified with ethereal hydrogen chloride to afford a colourless hygroscopic powder which was recrystallised from dichloromethane-diisopropylether to give the dihydrochloride as a colourless powder (0.36 g), m.p. 149.4° to 152.9° C.

The E-isomer was obtained as an oil and this was dissolved in acetonitrile and acidified with ethereal hydrogen chloride to afford a dihydrochloride as a colourless powder (0.71 g), m.p. 206.9° to 209.1° C. (The sample contained about 15% of the Z-isomer).

EXAMPLE 4

Methyl 4-[4-(2-methoxyphenyl)piperazin-1-yl]-3-phenylbutanoate

Magnesium turnings (1.64 g, 68.3 mmol) were added to a solution of E,Z-methyl 4-[4-(2-methoxyphenyl)piperazin-1-yl]-3-phenylbut-2-enoate (5.00 g, 13.7 mmol) in methanol (100 ml). The reaction mixture was placed in an ice-bath and slowly allowed to warm to room-temperature. After stirring for 4 h the reaction mixture was cooled (ice-water) and neutralised with ethereal hydrogen chloride. The solution was concentrated under reduced pressure and water (75 ml) added followed by basification with 2M-sodium hydroxide. The aqueous solution was washed with ethyl acetate (3×50 ml) and the combined organic phases washed with brine (50 ml), water (50 ml), dried (MgSO₄) and concentrated under reduced pressure. The crude product was chromatographed on silica gel, eluting with ethyl acetate: hexane (2:3 to 1:1) to afford the title compound as an oil (2.63 g).

EXAMPLE 5

4-[4-2-methoxyphenyl)piperazin-1-yl]-3-phenylbutanoic acid

Methyl 4-[4-(2-methoxyphenyl)piperazin-1-yl]-3-phenylbutanoate (2.63 g, 7.15 mmol) in concentrated hydrochloric acid (30 ml) was heated under reflux for 2 h and the reaction mixture concentrated under reduced pressure to afford a foam-like solid. The crude solid was triturated with acetone to afford the dihydrochloride salt of the title compound as an off-white powder (2.04 g) .

EXAMPLE 6

2,3,4,5,6,7-Hexahydro-1-[4-(4 -(2-methoxyphenyl)piperazin-1-yl)-3-phenylbutanoyl]-1H-azepine 1,1-Carbonydiimidazole (0.80 g, 4.9 mmol) was added to a solution of 4-[4-(2-methoxyphenyl)piperazin-1-yl]-3-phenylbutanoic acid dihydrochloride (2.00 g, 4.68 mmol) and triethylamine (0.95 g, 9.4 mmol) in dichloromethane (20 ml). After the cessation of gas evolution, a solution of azepine (0.51 g, 5.2 mmol) in dichloromethane (7 ml) was added and stirring continued overnight. The reaction mixture was concentrated under reduced pressure and the crude product chromatographed on silica gel, eluting with ethyl acetate: hexane (5:1) to afford an oil. The oil was dissolved in methyl acetate and acidified with ethereal hydrogen chloride to afford the title compound dihydrochloride hemihydrate as a colourless powder (1.08 g), m.p. 201.5–202.2 (dec.).

EXAMPLE 7

2,3,4,5,6,7-Hexahydro-1-[4-(4-(2-methoxyphenyl)piperazin-1-yl)-3-(2-pyridinyl)butanoyl]-1H-azepine Butyllithium, 1.6M solution in hexanes (4.5 ml, 7.2 mmol) was added dropwise to a solution of 1-(2-methoxyphenyl)-4-[2-(2-pyridyl)ethyl]piperazine (2.11 g, 7.10 mmol) in dry tetrahydrofuran (23 ml) at −70° under argon. After 30 min, a solution of 2,3,4,5,6,7-hexahydro-1-(2-chloro-ethanoyl]-1H-azepine (1.37 g, 7.8 mmol) in dry tetrahydrofuran (10.0 ml) was added dropwise. The reaction mixture was warmed to room temperature over 4 h and 2M-HCl (25 ml) added. The solution was concentrated in vacuo, washed with ethyl acetate (2×25 ml), basified with 2M-NaOH, and extracted with ethyl acetate (3×30 ml). The extracts were washed with brine (25 ml), water (25 ml), dried (MgSO$_4$) and concentrated in vacuo to afford an oil. Purification by chromatography on basic alumina, eluting with ether and then ethyl acetate, gave an oil which was dissolved in ethyl acetate-acetonitrile (4:1) and acidified with ethanol hydrogen chloride to afford an off white powder. The powder was recrystallised from ethyl acetate/acetonitrile to give the trihydrochloride salt of the product (0.58 g), m.p. 160.6°–161.3° C. (decomp).

(Found: C, 55.6; H, 7.6; N, 10.0. $C_{26}H_{36}N_4O_2.3HCl.\frac{3}{4}$ H$_2$O requires: C, 55.8; H, 7.3; N, 10.0%).

We claim:

1. A compound of the formula (I)

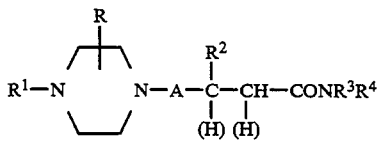

wherein
A is an alkylene chain of 1 or 2 carbon atoms optionally substituted by one or more lower alkyl groups,
R is hydrogen or lower alkyl,
$R^1$ is an aryl or a heteroaryl radical,
$R^2$ is an aryl radical, a heteroaryl radical, or an aryl- or heteroaryl-lower alkyl radical,
$R^3$ and $R^4$ together with the nitrogen atom to which they are both attached represent a saturated heterocyclic ring which may contain a further hetero atom, and the dotted line represents a single or double bond, the hydrogen atoms shown in brackets being present when the dotted line represents a single bond;
wherein aryl means phenyl or naphthyl optionally substituted by one or more substituents selected from lower alkoxy, (lower)alkylthio, halogen, trifluoromethyl, nitro, carbalkoxy, carboxamido, cyano, amino, (lower)alkylamino, and di(lower)alkylamino, and
heteroaryl means a monocyclic heteroaromatic radical containing 5 to 7 ring atoms or a bicyclic heteroaromatic radical containing 9 to 11 ring atoms, in which the heteroatoms are selected from one or two N atoms, one N atom and one O or S atom, and one O or S atom, and which is optionally substituted as for aryl.

2. A compound as claimed in claim 1 in which A is —CH$_2$— or —CH$_2$CH$_2$—.

3. A compound as claimed in claim 1 which is Z- or E-2,3,4,5,6,7-hexahydro-1-[4-(4-(2-methoxyphenyl)piperazin-1-yl)-3-phenylbut-2-enoyl]-1H-azepine, 2,3,4,5,6,7-hexahydro-1-[4-(4-(2-methoxyphenyl)piperazin-1-yl)-3-phenylbutanoyl]-1H-azepine, or 2,3,4,5,6,7-hexahydro-1-[4-(4-(2-methoxyphenyl)piperazin-1-yl)-3-(2-pyridinyl)butanoyl]-1H-azepine or a pharmaceutically acceptable salt thereof.

4. A pharmaceutical composition comprising a compound claimed in claim 1 in association with a pharmaceutically acceptable carrier.

* * * * *